(12) United States Patent
Butler et al.

(10) Patent No.: US 8,546,287 B2
(45) Date of Patent: Oct. 1, 2013

(54) RHENIUM PROMOTED CATALYST

(75) Inventors: James Butler, League City, TX (US); Olga Khabashesku, Houston, TX (US); Darek Wachowicz, Friendswood, TX (US); Callum Bailey, Humble, TX (US)

(73) Assignee: Fina Technology, Inc., Houston, TX (US)

( * ) Notice: Subject to any disclaimer, the term of this patent is extended or adjusted under 35 U.S.C. 154(b) by 457 days.

(21) Appl. No.: 12/790,917

(22) Filed: May 31, 2010

(65) Prior Publication Data

US 2011/0295048 A1    Dec. 1, 2011

(51) Int. Cl.
*B01J 29/06* (2006.01)
*B01J 27/182* (2006.01)

(52) U.S. Cl.
USPC ............ 502/78; 502/60; 502/73; 502/209; 502/214

(58) Field of Classification Search
USPC ................ 502/60, 73, 78, 209, 214
See application file for complete search history.

(56) References Cited

U.S. PATENT DOCUMENTS

| | | | |
|---|---|---|---|
| 3,436,174 A | 4/1969 | Sand | |
| 3,480,539 A | 11/1969 | Voorhies, Jr. et al. | |
| 3,819,736 A * | 6/1974 | Sato et al. | 585/475 |
| 3,832,449 A * | 8/1974 | Rosinski et al. | 423/705 |
| 4,086,186 A * | 4/1978 | Rubin et al. | 502/62 |
| 4,347,395 A * | 8/1982 | Chu et al. | 585/420 |
| 4,377,502 A * | 3/1983 | Klotz | 502/77 |
| 4,390,457 A * | 6/1983 | Klotz | 502/78 |
| 4,510,256 A * | 4/1985 | Zones | 502/62 |
| 4,619,820 A * | 10/1986 | Valyocsik | 423/708 |
| 5,670,131 A * | 9/1997 | Valyocsik | 423/702 |
| 6,008,425 A | 12/1999 | Mohr et al. | |
| 6,239,057 B1 * | 5/2001 | Ichikawa et al. | 502/66 |
| 6,398,947 B2 | 6/2002 | Beck et al. | |
| 6,426,442 B1 * | 7/2002 | Ichikawa et al. | 585/469 |
| 6,462,247 B1 | 10/2002 | Kelly et al. | |
| 6,562,752 B2 * | 5/2003 | Kasztelan | 502/216 |
| 7,273,828 B1 | 9/2007 | Boldingh et al. | |
| 7,332,454 B2 * | 2/2008 | Dang et al. | 502/60 |
| 2002/0045539 A1 | 4/2002 | Kasztelan | |
| 2003/0038058 A1 | 2/2003 | Acharya et al. | |
| 2004/0266608 A1 * | 12/2004 | Long et al. | 502/68 |
| 2006/0011514 A1 | 1/2006 | van den Berge et al. | |
| 2007/0299289 A1 | 12/2007 | Bresler et al. | |
| 2008/0064588 A1 * | 3/2008 | Boldingh et al. | 502/64 |
| 2008/0167178 A1 * | 7/2008 | Malyala et al. | 502/63 |
| 2009/0036296 A1 * | 2/2009 | Hu et al. | 502/78 |
| 2010/0298117 A1 | 11/2010 | Levin et al. | |

OTHER PUBLICATIONS

Y. Murakami et al. "Catalytic Activity of Noncloichiometric Niobium Oxide with Controlled Composition for Butene Isomerization," Bulletin of the Chemical Society of Japan, 61 2747-2752 (1988).

J. Haber, et al., "Manual of Methods and Procedures for Catalyst Characterization," International Union of Pure and Applied Chemistry, vol. 67 1260-1269, Nos. 8/9 (1995).

Kirk-Othmer, "Molecular Sieves," Encyclopedia of Chemical Technology, vol. 15 638-643 (3rd ed. 1981).

Pidco, et al "A comprehensive density functional theory study of ethane dehydrogenation over reduced extra-framework gallium species in ZSM-5 zeolite" Journal of Catalysis, vol. 240 73-84 (2006).

* cited by examiner

*Primary Examiner* — Elizabeth Wood

(57) ABSTRACT

A group V metal/rhenium-modified molecular sieve catalyst can be used in hydrocarbon conversion reactions. Embodiments can provide a toluene conversion of at least 30 wt % with selectivity to benzene above 40 wt % and to xylenes above 40 wt % and non-aromatics selectivity of less than 2.0 wt %.

12 Claims, 6 Drawing Sheets

Nb4% Mordenite

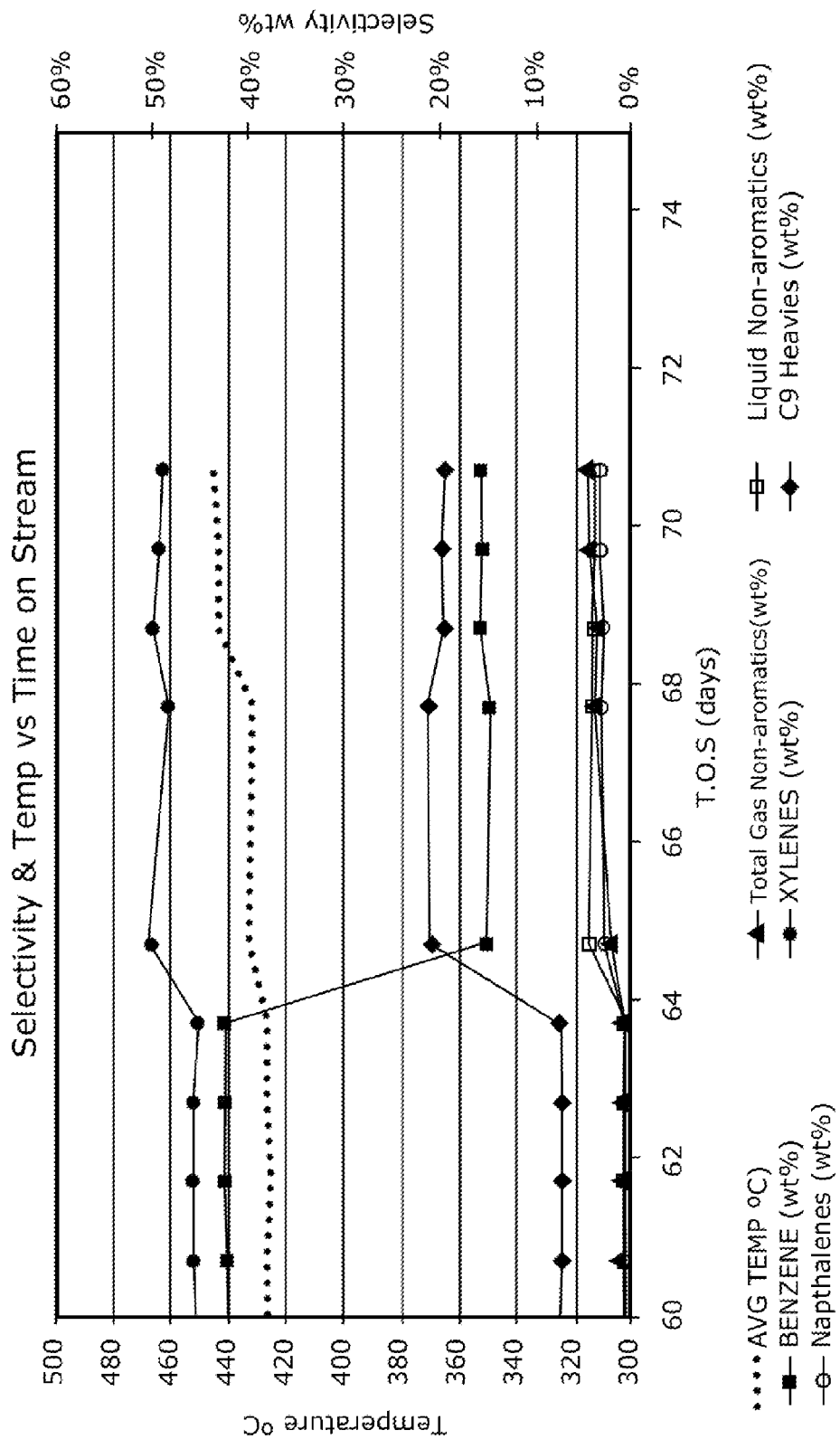

RHENIUM PROMOTED CATALYST

PCT/US11/38105 filed on May 26, 2011, which is published, claims the benefit of the present Application.

FIELD

The present invention generally relates to the disproportionation of alkylaromatic feedstreams.

BACKGROUND

The disproportionation of toluene involves a well known transalkylation reaction in which toluene is converted to benzene and xylene, often referred to as a Toluene Disproportionation Process or TDP, in accordance with the following reaction:

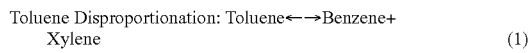

Toluene Disproportionation: Toluene⇌Benzene+
   Xylene      (1)

Mordenite is one of a number of molecular sieve catalysts useful in the transalkylation of alkylaromatic compounds. TDP mordenite catalysts generally require a sulfiding procedure to be carried out prior to their use, in order to avoid the initial high percentage of non-aromatics in the product stream. Such non-aromatics can be hard to remove from the product stream because they boil at around the same conditions as benzene.

It is desirable to increase efficiency of the toluene disproportionation process. Longer run times and fewer process shutdowns increase production efficiency and lower associated costs, and this increase in efficiency can be achieved in part by lowering operating temperatures. In view of the above, it would be desirable to have a process of conducting toluene disproportionation with lower production of non-aromatic compounds, with a catalyst with increased activity that can be operated at lower temperatures.

SUMMARY

Embodiments of the present invention generally include a rhenium-modified molecular sieve catalyst, used in the conversion of hydrocarbons. The molecular sieve catalyst can include a group V metal and rhenium as promoters. The group V metal can be niobium deposited on the catalyst support. The niobium can come from precursors that are water-soluble such as chosen from the group of niobium oxalate and ammonium niobate(V) oxalate. The rhenium deposited on the catalyst support can come from precursors that are likewise water-soluble, such as chosen from the group of sodium perrhenate, ammonium perrhenate, and dirhenium decacarbonyl. Embodiments of the catalyst can be capable of regeneration by coke burnout without substantial activity loss.

In one embodiment, the molecular sieve is a zeolite. In another embodiment, the zeolite is mordenite.

In one embodiment, the conversion of hydrocarbons consists of a transalkylation reaction, comprising the disproportionation of $C_7$ to $C_{12}$ alkylaromatics. In one embodiment, the reaction is a toluene disproportionation reaction (TDP).

In one embodiment, a toluene disproportionation reaction results in at least a 30 wt % toluene conversion of the toluene feed. In another embodiment, the reaction results in less than 2.0 wt % non-aromatic products of the reaction product stream composition, not considering unreacted toluene. In another embodiment, the reaction results in less than 1.0 wt % non-aromatic products of the reaction product stream composition, not considering unreacted toluene.

An alternate embodiment of the present invention is a process for disproportionation of toluene to benzene and xylene that includes passing a toluene/hydrogen feedstock over a rhenium-modified molecular sieve catalyst at reaction conditions sufficient to provide toluene conversion of at least 30 wt % of the toluene feed. The process can provide non-aromatic selectivity of less than 2.0 wt % of the reaction product stream composition. The rhenium content of the catalyst can be between 0.0002 wt % to 1.0 wt % by weight rhenium metal on the catalyst. The rhenium can come from a rhenium precursor chosen from the group consisting of water-soluble rhenium compounds. The molecular sieve catalyst can further include a group V metal as a promoter. The group V metal can be niobium deposited on the catalyst support. The niobium can come from precursors that are water-soluble such as chosen from the group of niobium oxalate and ammonium niobate(V) oxalate. The reaction temperature can be between 150° C. and 500° C., optionally between 300° C. and 400° C. Embodiments of the process can include the regeneration by coke burnout of the catalyst without substantial activity loss.

BRIEF DESCRIPTION OF DRAWINGS

FIG. 6 is a graph showing selectivity to certain products for a Nb(3 wt %)/Re(0.1 wt %)-Mordenite catalyst when a Toluene feedstream is changed to a 50:50 Toluene:Atosol feed.

DETAILED DESCRIPTION

Figure 1:
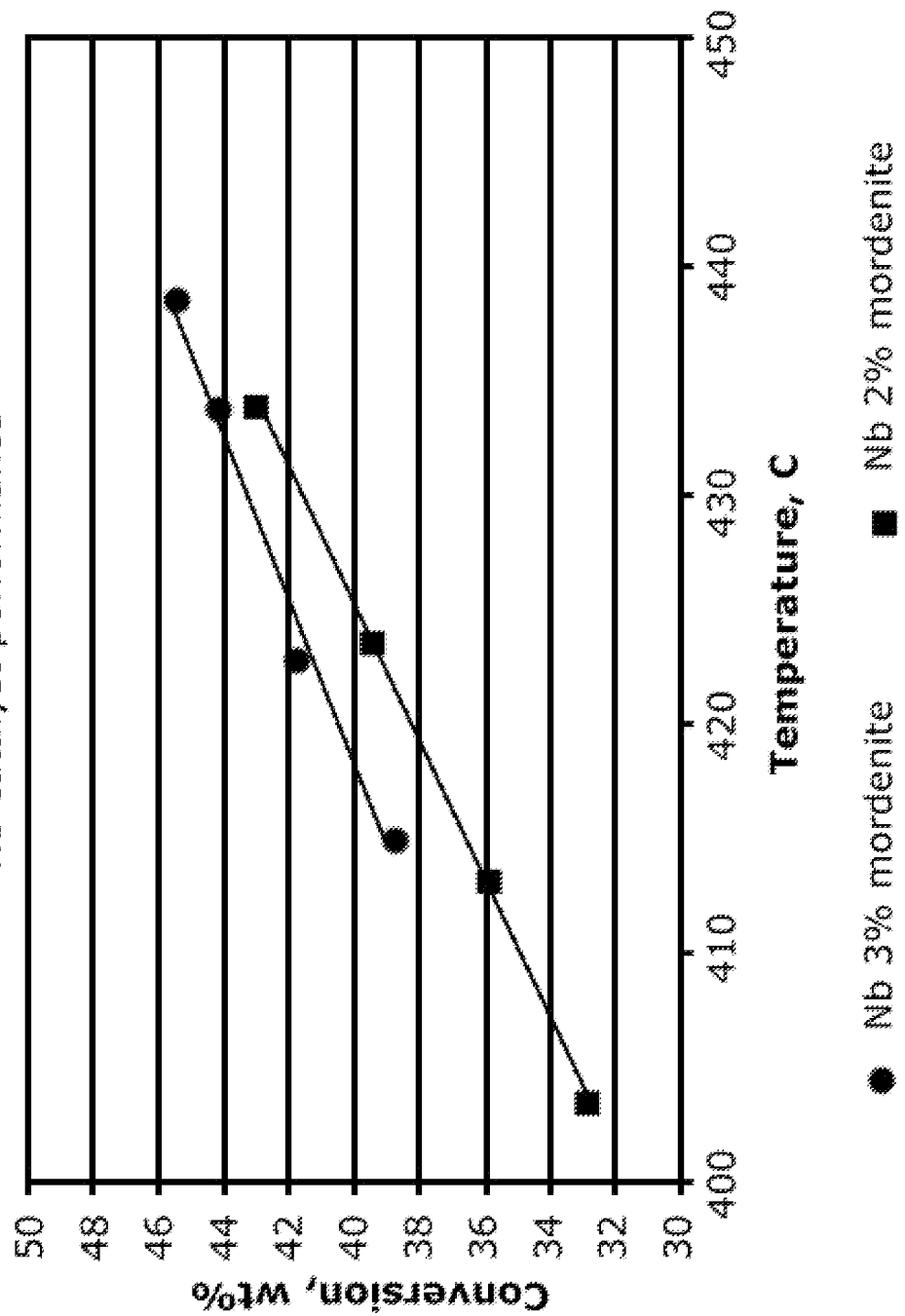
FIG. 1 is a graph of conversion versus temperature for two Nb-Mordenite catalysts.

The catalyst of the present invention can include a molecular sieve. The molecular sieve of the present invention can include any molecular sieve having a pore size of a sufficient size to admit alkyl aromatic hydrocarbons. In an embodiment, the molecular sieve is selected from the group of a zeolite, faujasites, crystalline silicoaluminophosphates (SAPO), and aluminophosphates (ALPO). In a more specific embodiment, the molecular sieve is a zeolite.

Mordenite is a crystalline aluminosilicate zeolite exhibiting a network of silicon and aluminum atoms interlinked by oxygen atoms within the crystalline structure. For a general description of mordenite catalysts, reference is made to Kirk-Othmer, Encyclopedia of Chemical Technology, 3rd Edition, 1981, under the heading "Molecular Sieves", Vol. 15, pages 638-643, which is incorporated by reference herein. Mordenite, as found in nature or as synthesized to replicate the naturally occurring zeolite, typically exhibits a relatively low silica-to-alumina mole ratio of about 10 or less. Also known, however, are mordenite catalysts exhibiting substantially lower alumina content. These alumina deficient mordenite catalysts exhibit silica-to-alumina ratios greater than 10, ranging up to about 100, and may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al, both of which are incorporated by reference herein. Both the typical and the aluminum deficient mordenites are known to be useful in the disproportionation of toluene.

Disproportionation of toluene feedstock may be performed at temperatures ranging from 150° C. to 600° C. or above. Optionally the temperature can range from 200° C. to 500° C., or from 250° C. to 450° C. Toluene disproportionation may be at pressures ranging from atmospheric to 1500 psig or above, optionally from 200 psig to 1000 psig, optionally from 400 psig to 800 psig. The liquid hourly space velocities (LHSV) can range from around 1 $hr^{-1}$ to 10 $hr^{-1}$, optionally 2 $hr^{-1}$ to 8 $hr^{-1}$, and optionally 3 $hr^{-1}$ to 6 $hr^{-1}$. The specific catalyst, however, may impose constraints on reaction temperatures in terms of catalyst activity and aging characteristics. In general relatively high temperatures are used when employing the high alumina mordenites (low silica-to-alumina ratios) and somewhat lower temperatures when employing the low alumina mordenites (high silica-to-alumina ratios). Accordingly, where mordenite catalysts exhibiting high silica/alumina ratios have been employed in the transalkylation of alkylaromatics, it has been the practice to operate toward the lower end of the temperature range.

Hydrogen is generally supplied along with toluene to the reaction zone. While the disproportionation reaction (1) does not involve chemical consumption of hydrogen, the use of a hydrogen co-feed is generally considered to prolong the useful life of the catalyst. The amount of hydrogen supplied, which normally is measured in terms of the hydrogen/toluene mole ratio, is generally shown in the prior art to increase as temperature increases. The hydrogen:toluene mole ratio can generally range from 0.05:1 to 5:1, optionally from 0.5:1 to 4:1, optionally from 1:1 to 3:1.

A catalyst comprising a substrate that supports a promoting metal or a combination of metals can be used to catalyze hydrocarbon reactions. The method of preparing the catalyst, pretreatment of the catalyst, and reaction conditions can influence the conversion, selectivity, and yield of the reactions.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%. If more than one promoter is combined, they together generally can range from 0.01% up to 70% by weight of the catalyst. The elements of the catalyst composition can be provided from any suitable source, such as in its elemental form, as a salt, as a coordination compound, etc.

In one embodiment, the catalyst can be prepared by combining a substrate with at least one promoter element. Embodiments of a substrate can be a molecular sieve, from either natural or synthetic sources. Zeolites can be an effective substrate, can be commercially available, and are well known in the art. Alternate molecular sieves also contemplated are zeolite-like materials such as for example faujasites, crystalline silicoaluminophosphates (SAPO) and the aluminophosphates (ALPO).

The present invention is not limited by the method of catalyst preparation, and all suitable methods should be considered to fall within the scope herein. Particularly effective techniques are those utilized for the preparation of solid catalysts wherein a molecular sieve is used as a substrate and one or more promoter elements are added. Conventional methods include co-precipitation from an aqueous, an organic, or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition can be calcined in the presence of a free oxygen-containing gas, usually at temperatures between about 300° C. and about 900° C. for from 1 to 24 hours. The calcination can be in an oxygen-containing atmosphere, or alternately in a reducing or inert atmosphere.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

The prepared catalyst can be ground, pressed, sieved, shaped and/or otherwise processed into a form suitable for loading into a reactor. The reactor can be any type known in the art, such as a fixed bed, fluidized bed, or swing bed reactor. Optionally an inert material, such as quartz chips, can be used to support the catalyst bed and to place the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 150° C. to 500° C., or optionally down to atmospheric or other desired temperature. The reactor can be kept under an inert purge, such as under a nitrogen or helium purge.

TDP mordenite catalysts generally require a sulfiding procedure to be carried out prior to their use, in order to avoid an initial high percentage of non-aromatics. Such non-aromatics can be hard to remove from the product stream because they can boil at approximately the same conditions as benzene.

Sulfiding consists of the process of depositing sulfur on the catalyst. Sulfiding is known in the art and all suitable sulfiding methods should be considered to fall within the scope herein. A generalized sulfiding procedure involves a sulfur-bearing agent and hydrogen in contact with the catalyst at an elevated temperature. The hydrogen reacts with the sulfur-bearing agent to produce hydrogen sulfide ($H_2S$), which serves as the sulfiding medium. The $H_2S$ reacts with the metallic catalyst, which gives up an oxygen to form water. The sulfur replaces the oxygen on the catalyst. The process generally follows a schedule of four stages that include: a) placing the catalyst and a sulfur-bearing agent, such as dimethyl sulfide or dimethyl sulfoxide, in a reactor that is purged of air and dehydrated, with or without vacuum, temperature can be in the range of 120° C. to 150° C.; b) hydrogen is introduced with the catalyst and sulfur-bearing agent and the temperature is increased, for example to 230° C.; c) sulfiding occurs in an atmosphere of $H_2S$, temperature can be in the range of 230° C. to 260° C.; d) sulfiding continues in an atmosphere of $H_2S$ at an elevated temperature, such as in the range of 270° C. to 290° C. A minimum of four hours is typically necessary to complete the sulfiding process. In one example the steps of b), c) and d) each take approximately two hours to complete.

The use of Ni/Mordenite molecular sieve catalysts in toluene disproportionation and heavy aromatic conversion reactions is well known in the art. The present invention provides an improved means of conducting these reactions wherein the nonaromatic selectivity is comparable or lower than the currently used Ni/Mordenite catalyst, even without sulfiding.

In accordance with the present invention, there is provided a novel process for the disproportionation of toluene over a metal promoted molecular sieve catalyst in which a niobium and rhenium modified mordenite catalyst is used, resulting in low amounts of nonaromatics, and allowing for operation at lower temperatures and longer process run times. Nb—Re/mordenite catalysts can produce an initial low percentage of liquid non-aromatics even without the use of a sulfiding procedure.

One embodiment of the present invention is a molecular sieve catalyst containing rhenium useful in the conversion of hydrocarbons. In an embodiment the molecular sieve catalyst contains at least 0.0002 wt % rhenium calculated as metallic metal based on the weight of the total catalyst-reagent. In an alternate embodiment the molecular sieve catalyst contains at least 0.002 wt % rhenium. In another alternative embodiment, the molecular sieve catalyst contains at least 0.02 wt % rhenium. In another embodiment the molecular sieve catalyst contains up to 0.1 wt %, or up to 0.2 wt %, or optionally up to 0.3 wt % or more rhenium. In each embodiment, the wt % of the rhenium is calculated as metallic metal based on the weight of the total catalyst-reagent. The molecular sieve catalyst can be of any suitable kind, such as one having a substrate of a zeolite or a faujasite.

One embodiment of the present invention is a molecular sieve catalyst containing a group V metal, such as niobium, and rhenium useful in the conversion of hydrocarbons. In an embodiment the molecular sieve catalyst contains at least 0.005 wt % niobium and at least 0.0002 wt % rhenium calculated as metallic metal based on the weight of the total catalyst-reagent. In an alternate embodiment the molecular sieve catalyst contains at least 0.05 wt % niobium and at least 0.002 wt % rhenium. In another alternative embodiment, the molecular sieve catalyst contains at least 0.5 wt % niobium and at least 0.02 wt % rhenium. In another embodiment the molecular sieve catalyst contains up to 2 wt %, or up to 3 wt %, or optionally up to 5 wt % or more niobium and up to 0.1 wt %, or up to 0.2 wt %, or optionally up to 0.3 wt % or more rhenium. In each embodiment, the wt % of the rhenium and niobium is calculated as metallic metal based on the weight of the total catalyst-reagent. The molecular sieve catalyst can be a zeolite, and can be a mordenite zeolite.

The precursor for the niobium can be chosen from among water-soluble compounds that contain niobium. The precursor for the niobium can be chosen from among the following compounds: niobium oxalate hydrate and ammonium niobate (V) oxalate hydrate, as well as any combinations thereof. Niobium containing water-soluble precursors allow for more evenly distributed and accurate niobium loading. These precursors can also allow for higher niobium loadings, which in turn allow for TDP to be operated at lower temperatures, thus delaying catalyst deactivation, maximizing run time and limiting the need for process shutdowns.

The precursor for the rhenium can be chosen from among any suitable compounds that contain rhenium. The precursor for the rhenium can be chosen from among water-soluble compounds that contain rhenium. The precursor for the rhenium can be chosen from among the following compounds: sodium perrhenate, ammonium perrhenate, and dirhenium decacarbonyl, as well as any combinations thereof. Rhenium containing water-soluble precursors allow for more evenly distributed and accurate rhenium loading.

The catalyst of the present invention can be used in transalkylation reactions, such as the disproportionation of an alkyl benzene or mixtures of alkyl benzenes to produce benzene and polyalkyl benzene. For instance, the invention can be used in the disproportionation of relatively heavy aromatics, such as $C_8$ to $C_{12}$ alkyl aromatics. The invention is particularly suitable for the disproportionation of toluene, which can optionally be carried out in the presence of heavier alkylaromatics. In an embodiment when used in a toluene disproportionation reaction process, the present invention can provide a toluene conversion of at least 30 wt % of the toluene feed or in an alternate embodiment a toluene conversion of at least 40 wt % of the toluene feed. In an embodiment when used in a toluene disproportionation reaction process, the present invention can provide a non-aromatic selectivity of less than 2.0 wt % of the reaction product stream composition, not including unreacted toluene feed. In an embodiment when used in a toluene disproportionation reaction process, the present invention can provide a non-aromatic selectivity of less than 1.0 wt % of the reaction product stream composition, not including unreacted toluene feed. Toluene conversion represents the fraction (percentage) of toluene in the feed that is reacted to form reacted toluene molecules. Non-aromatic selectivity represents the fraction (percentage) of reacting toluene molecules that produce non-aromatic compounds.

An alternate embodiment of the present invention is a process for disproportionation of toluene to benzene and xylene that includes passing a toluene/hydrogen feedstock over a rhenium promoted mordenite catalyst at reaction conditions sufficient to provide toluene conversion of at least 30 wt % of the toluene feed and provide non-aromatic selectivity of less than 1.0 wt % of the reaction product stream composition. The rhenium precursor can be chosen from sodium perrhenate, ammonium perrhenate, or dirhenium decacarbonyl or combinations thereof. The rhenium content of the catalyst can be of from 0.0002 wt % to 0.2 wt %. In an embodiment the toluene conversion is at least 40 wt % of the toluene feed. The non-aromatic selectivity can be less than 2.0 wt % of the reaction product composition, optionally less than 1.0 wt %, optionally less than 0.85 wt %, and optionally less than 0.75 wt %. In an embodiment the selectivity to benzene is at least 30 wt % of the reaction product composition, optionally at least 35 wt %, optionally at least 40 wt %. In an embodiment of the invention the selectivity to xylene is at least 30 wt % of the reaction product composition, optionally at least 35 wt %, optionally at least 40 wt %. In an embodiment the selectivity to heavies is less than 20 wt % of the reaction product composition, optionally less than 15 wt %, optionally less than 10 wt %.

An alternate embodiment of the present invention is a process for disproportionation of toluene to benzene and xylene that includes passing a toluene/hydrogen feedstock over a rhenium promoted mordenite catalyst at reaction conditions sufficient to provide toluene conversion of at least 30 wt % of the toluene feed and provide non-aromatic selectivity of less than 2.0 wt % of the reaction product composition. In an embodiment the toluene conversion is at least 45 wt % of the toluene feed. The non-aromatic selectivity can be less than 1.0 wt % of the reaction product composition, optionally less than 0.75 wt %. In an embodiment the selectivity to benzene is at least 30 wt % of the reaction product composition, optionally at least 35 wt %, optionally at least 40 wt %. In an embodiment of the invention the selectivity to xylene is at least 30 wt % of the reaction product composition, optionally at least 35 wt %, optionally at least 40 wt %. In an embodiment the selectivity to heavies is less than 20 wt % of the reaction product composition, optionally less than 15 wt %, optionally less than 10 wt %.

In an embodiment the reaction temperature can range from 150° C.-500° C., optionally from 200° C.-450° C., optionally from 300° C.-400° C. The temperature can be adjusted to maintain a certain toluene conversion level, such as 30 wt % of the toluene feed, or optionally 40 wt %, or more. The hydrogen:toluene molar ratio can be between 0.05:1 to 5:1, optionally from 0.5:1 to 4:1, optionally from 1:1 to 3:1. The reaction pressure can range between atmospheric to 1500 psig or above, optionally from 100 psig to 1000 psig, optionally from 200 psig to 800 psig. The LHSV can be from 1 hr$^{-1}$ to 10 hr$^{-1}$, optionally 1 hr$^{-1}$ to 7 hr$^{-1}$, and optionally 1 hr$^{-1}$ to 4 hr$^{-1}$.

In yet another embodiment of the present invention a process for disproportionation of toluene to benzene and xylene includes passing a toluene/hydrogen feedstock over a combined niobium-modified and rhenium-modified mordenite catalyst with a niobium content of the catalyst of at least 0.05 wt % and a rhenium content of the catalyst of at least 0.002 wt %. The reaction conditions are sufficient to provide toluene conversion of at least 30 percent and include a reaction temperature between 150° C. and 500° C. and reaction pressure between 200 psig to 800 psig. The non-aromatic selectivity is less than 2.0 wt % of the reaction product composition and the process is capable of such conversion for at least 25 days.

EXAMPLES

Example 1

Three Nb/Mordenite catalysts containing 2 wt %, 3 wt %, and 4 wt % of niobium, respectively, were prepared and used in experimental TDP runs. Zeolyst Mordenite Extrudate was used as the base material and was impregnated with niobium using an insipient wetness impregnation technique. The niobium precursor used was ammonium niobate oxalate. For each catalyst, ammonium niobate oxalate hydrate dissolved in 13.5 g of water was deposited on 30 g of mordenite extrudate support. For a 2 wt % loading, 2.537 g of ammonium niobate oxalate hydrate was used. For a 3 wt % loading, 3.806 g of ammonium niobate oxalate hydrate was used. For a 4 wt % loading, 5.075 g of ammonium niobate oxalate hydrate was used. The aqueous solutions were added dropwise to the mordenite base with mixing. The volume of the solution was calculated based on mordenite pore volume per gram of support such that no moisture was present at the bottom of the dish after the impregnation was completed. The support was dried at 120° C. overnight and calcined at 550° C. for 5 hours.

An example of the preparation procedure for obtaining 3 wt % Nb Mordenite by insipient wetness impregnation is now given. Mordenite extrudate (Zeolyst) and ammonium niobate (V) oxalate hydrate (Aldrich), 99.99% trace metals basis $C_4H_4NNbO_9 \cdot xH_2O$ and Molecular Weight 302.98 (anhydrous basis), were used for the catalyst preparation. 30 g of Mordenite zeolite was dried in an oven at 110° C. overnight. Void volume of Mordenite extrudate was determined as 0.45 cc/g, which corresponds to 13.5 cc of solution that was needed for insipient impregnation of 30 g of mordenite extrudate. 3.806 g of ammonium niobate oxalate hydrate was placed in a beaker with 13.5 ml of deionized water. A milky suspension formed after the addition of ammonium niobate oxalate, but the mixture clarified upon standing without mixing overnight and produced a clear solution. (In another experiment a clear solution was obtained by heating the mixture gently without stirring at ~40° C. for about 20 minutes.) The Nb containing solution was added dropwise with slow mixing to the mordenite placed in the porcelain dish. No solution was left at the bottom of the dish after impregnation; solution was completely absorbed by the mordenite.

The impregnated catalysts were evaluated in a lab scale reactor for disproportionation of toluene to benzene and xylene. The testing conditions are summarized in Table 1:

TABLE 1

| Reactor - down flow | Niobium - Mordenite catalyst Nb 2 wt %, 3 wt %, 4 wt % |
|---|---|
| Feed | Toluene |
| LHSV | 4/hr |
| H$_2$/HC molar ratio | 2:1 |
| Temperature | Adjusted to hold constant conversion |
| RX Inlet Pressure | 600 psig |
| Target conversion | >40% (<60% toluene in effluent) |
| Catalyst volume | 30 mL |

Each new catalyst was loaded into the reactor at the amount of 22 g, which corresponded to 30 cc volume. The reactor was flushed with flowing nitrogen for 15 minutes and pressure checked. The reactor was switched to hydrogen flow at 1 L/min and the pressure increased to 600 psig. The temperature was ramped at 20° C./hr to 360° C. (680° F.), and then the feed was switched to toluene. No sulfiding was done. The temperature was adjusted slowly attempting to maintain about a 40-45 wt % conversion of toluene.

Table 2 shows the activity and temperatures for the three Nb/mordenite catalysts.

TABLE 2

| Nb 2 wt % Mordenite | | | Nb 3 wt % Mordenite | | | Nb 4 wt % Mordenite | | |
| --- | --- | --- | --- | --- | --- | --- | --- | --- |
| Time on Stream days | Toluene conversion % | Temp ° C. | TOS days | Toluene conversion % | Temp ° C. | TOS days | Toluene conversion % | Temp ° C. |
| 0 | 32.2 | 383 | 3 | 50.9 | 440 | 1 | 41.8 | 385 |
| 1 | 30.6 | 388 | 4 | 38.8 | 415 | 2 | 42.2 | 396 |
| 2 | 32.0 | 388 | 5 | 41.7 | 423 | 5 | 44.7 | 406 |
| 3 | 36.5 | 398 | 6 | 44.2 | 434 | 7 | 41.6 | 407 |
| 12 | 34.4 | 393 | 7 | 45.5 | 439 | 11 | 42.3 | 418 |
| 13 | 32.7 | 393 | 10 | 44.7 | 449 | 12 | 45.9 | 428 |
| 14 | 33.8 | 398 | 11 | 45.3 | 449 | 13 | 46.2 | 436 |
| 17 | 32.8 | 403 | 12 | 45.0 | 452 | 14 | 47.6 | 441 |
| 18 | 35.8 | 412 | 13 | 45.3 | 452 | 15 | 46.9 | 444 |
| 19 | 39.4 | 424 | 14 | 44.4 | 452 | 16 | 49.2 | 449 |
| 20 | 42.9 | 434 | | | | 19 | 47.0 | 449 |
| | | | | | | 20 | 46.3 | 452 |
| | | | | | | 23 | 42.7 | 444 |
| | | | | | | 25 | 43.1 | 454 |

For the Nb 2 wt % Mordenite catalyst the toluene conversion was about 38% at a temperature of about 420° C. For the Nb 3 wt % Mordenite catalyst the toluene conversion was about 41% at a temperature of about 420° C. FIG. 1 displays graphically the toluene conversion and reaction temperatures for the Nb 2 wt % Mordenite catalyst and the Nb 3 wt % Mordenite catalyst.

For the Nb 4 wt % Mordenite catalyst the toluene conversion was about 43% at a temperature of about 420° C. Table 3, below, shows toluene conversion and selectivity to benzene, xylenes, liquid non-aromatics and $C_9+$ heavies over the Nb 4 wt % Mordenite catalyst.

TABLE 3

| TOS Days | CONV wt % | Benzene wt % | Xylenes wt % | Heavies wt % | Liq. Non-ar wt % | Temp C. |
| --- | --- | --- | --- | --- | --- | --- |
| 1 | 41.84 | 44.18 | 46.35 | 7.76 | 0.41 | 385.4 |
| 2 | 42.21 | 44.61 | 45.95 | 8.02 | 0.41 | 395.5 |
| 5 | 44.68 | 44.71 | 46.21 | 7.84 | 0.45 | 405.6 |
| 7 | 41.62 | 44.61 | 46.42 | 7.77 | 0.42 | 407.4 |
| 11 | 42.35 | 44.71 | 45.53 | 8.27 | 0.54 | 417.9 |
| 12 | 45.94 | 43.61 | 45.45 | 9.22 | 0.57 | 428.2 |
| 13 | 46.18 | 44.25 | 44.55 | 9.32 | 0.62 | 435.6 |
| 14 | 47.60 | 44.69 | 44.02 | 9.34 | 0.61 | 440.7 |
| 15 | 46.92 | 43.76 | 44.19 | 9.55 | 0.55 | 443.8 |
| 16 | 49.16 | 42.59 | 44.63 | 10.64 | 0.63 | 448.8 |
| 19 | 46.98 | 43.18 | 44.19 | 9.61 | 0.63 | 448.9 |
| 20 | 46.27 | 43.10 | 44.36 | 9.56 | 0.65 | 451.9 |
| 23 | 42.71 | 43.21 | 45.47 | 8.98 | 0.71 | 443.9 |
| 25 | 43.10 | 42.84 | 44.99 | 9.49 | 0.62 | 454.5 |
| Average | 44.83 | 43.86 | 45.16 | 8.96 | 0.56 | 429.2 |

Figure 2:
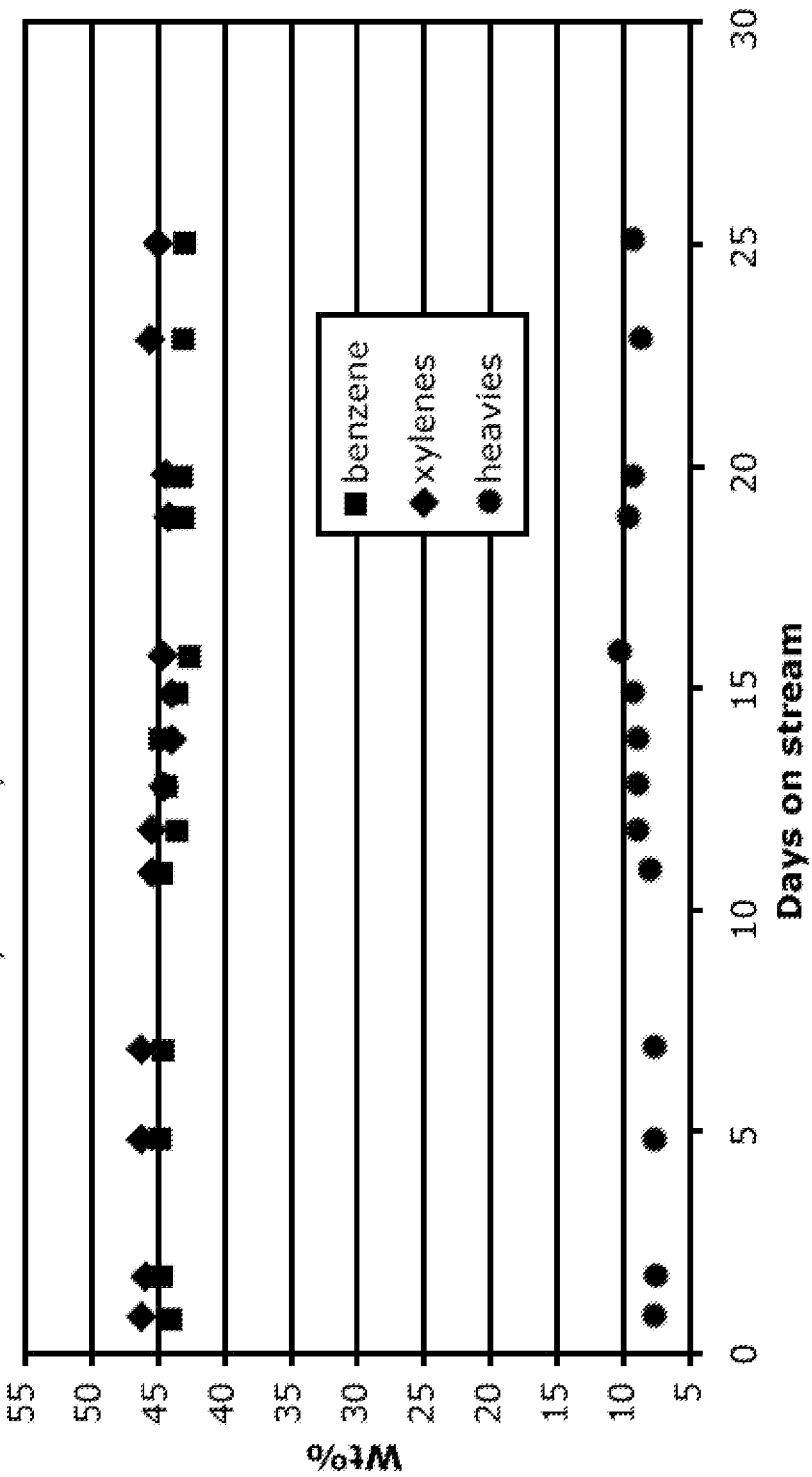
FIG. 2 is a graph showing selectivity to certain products for a Nb(4 wt %)-Mordenite catalyst.
Figure 3:
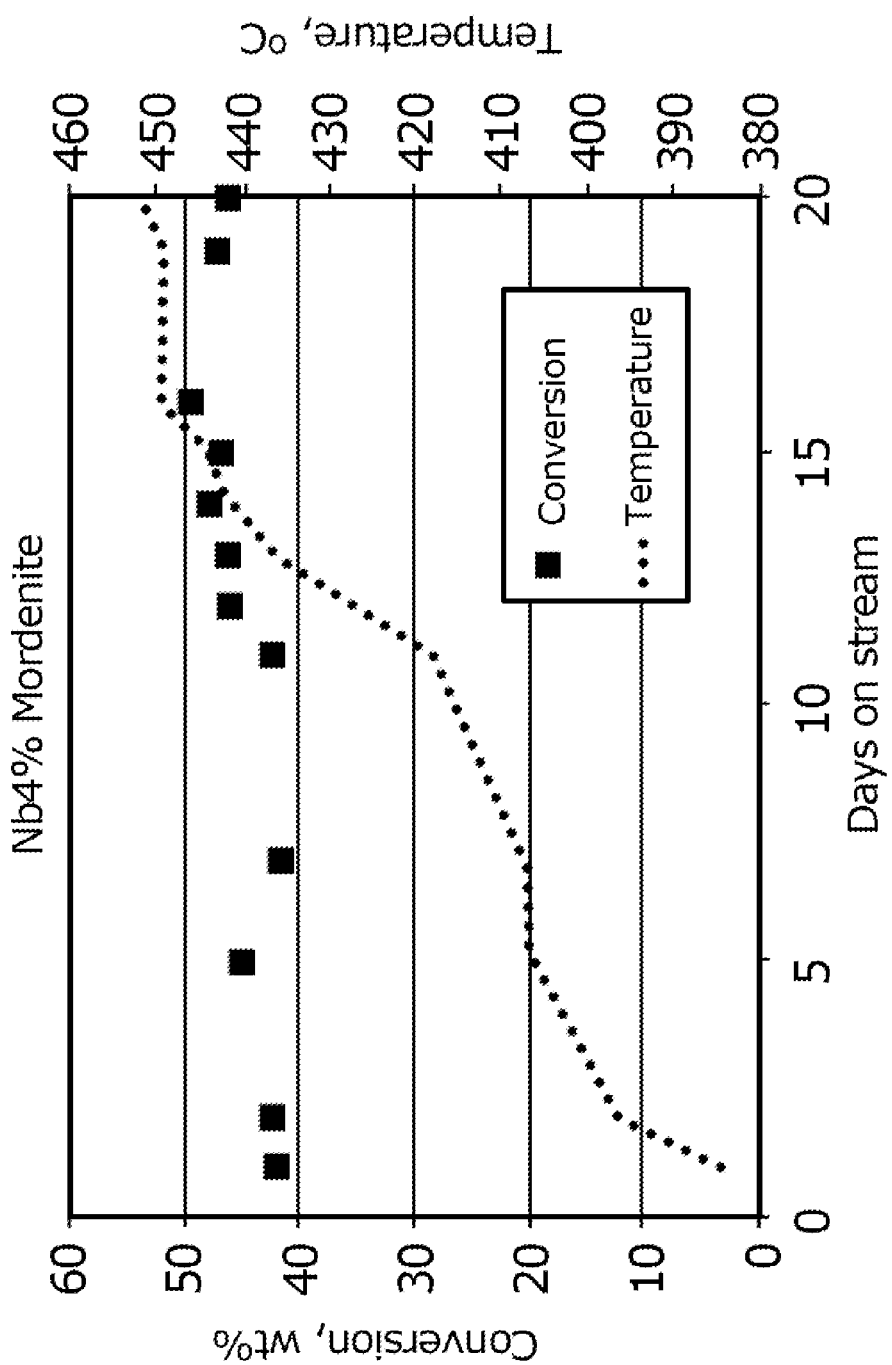
FIG. 3 is a graph showing toluene conversion and reaction temperature for a Nb(4 wt %)-Mordenite catalyst.

The aromatic selectivities were within expected ranges, on average 43.9 wt % for benzene, 45.2 wt % for xylenes and 9.0 wt % for heavies. FIG. 2 displays graphically the selectivity to benzene, xylene, and $C_9+$ heavies for the Nb 4 wt % Mordenite catalyst. FIG. 3 displays graphically the toluene conversion and reaction temperature for the Nb 4 wt % Mordenite catalyst.

Example 2

A Nb—Re/Mordenite catalyst containing 3 wt % of niobium and 0.1 wt % of rhenium was prepared and used in experimental TDP runs. Zeolyst Mordenite Extrudate was used as the base material and was impregnated with niobium. The niobium precursor used was niobium pentachloride. 2.61 g of niobium pentachloride was dissolved in 13.5 ml of ethanol and deposited on 30 g of mordenite extrudate support. The ethanol solution was added dropwise to the mordenite base with mixing. The volume of the solution was calculated based on mordenite pore volume per gram of support such that no moisture was present at the bottom of the dish after the impregnation was completed. The support was dried at 120° C. overnight and calcined at 550° C. for 5 hours. Rhenium was added by dissolving 0.0432 g of ammonium perrhenate in 13.5 ml of water. The aqueous solution was added dropwise to the 3% Nb/Mordenite catalyst. The catalyst was dried at 120° C. overnight and calcined at 550° C. for 3 hours, resulting in a catalyst having 3 wt % Nb and 0.1 wt % Re by weight of total catalyst. No sulfiding was done.

The resulting Nb 3 wt %-Re 0.1 wt. % mordenite catalyst was contacted with a toluene feed. The toluene feed was started at a set temperature 370° C. and the average bed temperature was 364.5° C. The catalyst was on stream with a toluene feed for 63 days. During this time period, the experiment was interrupted three times due to shutdowns on days 11 to 14, 19 and 21 to 24. After the third shutdown, the catalyst was regenerated at reaction temperature with a hydrogen flow of 1 liter/min for 24 hours.

After the regeneration the feed was restarted at a lower temperature than that before the shutdown, indicating that the catalyst is capable of regeneration by coke burnout without substantial activity loss. At 420° C. the conversion of toluene stabilized at a 47% level. During the last 30 days of the run the temperature required only minor adjustments, mostly due to pump rate fluctuations.

Figure 4:
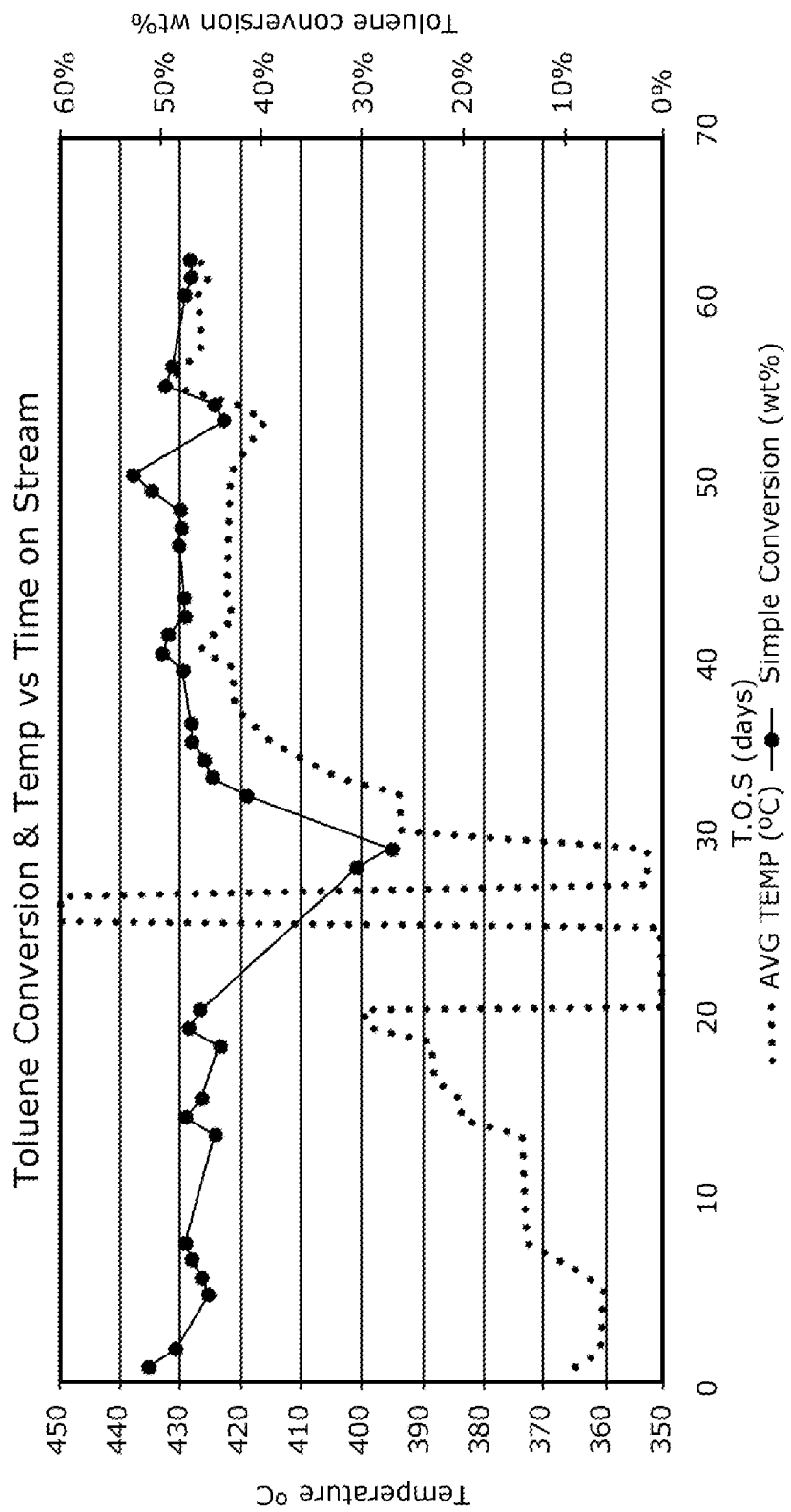
FIG. 4 is a graph showing toluene conversion and reaction temperature over time for a Nb(3 wt %)/Re(0.1 wt %)-Mordenite catalyst with a Toluene feedstream.

The use of the Nb 3 wt %-Re 0.1 wt. % mordenite catalyst has shown a noticeable improvement over the comparable 3% Nb-mordenite catalyst of Example 1. In Example 1, the average conversion was about 45% under temperatures of about 450° C. For the Nb/Re-mordenite catalyst, a graph of toluene conversion vs. time on stream is shown in FIG. 4. As indicated in FIG. 4, the conversion of toluene the 3% Nb/Re-mordenite catalyst stabilized at a 47% level under temperatures of about 420° C., in contrast to the Nb-mordenite catalysts of Example 1 in which the conversion of toluene at about 420° C. was about 38% for the 2 wt % Nb-mordenite catalyst, about 41% for the 3 wt % Nb-mordenite catalyst, and about 43% for the 4 wt % Nb-mordenite catalyst. The use of the rhenium promoted Nb-mordenite catalyst over the Nb-mordenite catalyst, therefore, can result in an increase in conversion under the same temperatures. The use of the rhenium promoted mordenite catalyst showed an increase of about 6 wt % conversion of toluene in the feed in the present example.

Figure 5:
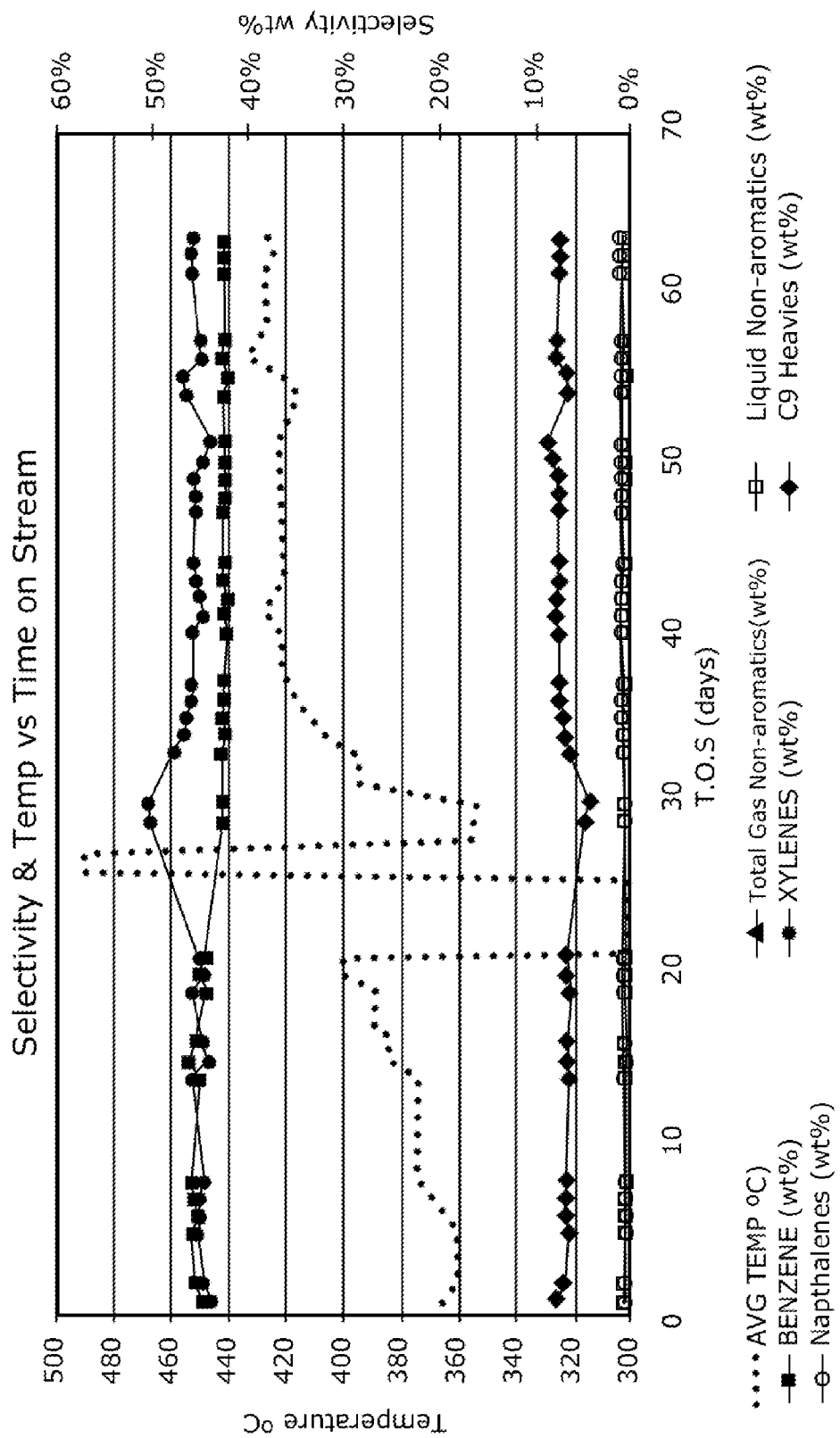
FIG. 5 is a graph showing selectivity to certain products for a Nb(3 wt %)/Re(0.1 wt %)-Mordenite catalyst with a Toluene feedstream.

FIG. 5 depicts a graph of selectivities to major products and heavies. As indicated in FIG. 5, liquid non-aromatics were found to be in the range of from 0.34 wt % to 0.92 wt % and naphthalenes were found to be in the range of from 0.540 wt % to 1.007 wt %. As also indicated in FIG. 5, the ratio of Benzene-to-Xylenes was about 0.94 during the period of stable conversion at 47%. Also, a p-Xylene/Xylenes ratio of 0.24 was observed during the run of Example 2.

Example 3

The run of Example 2 was altered to switch the Toluene feed to a 50:50 Toluene:Atosol feed to observe the performance of the Nb 3 wt %-Re 0.1 wt. % mordenite catalyst for a feed with a lower grade of toluene. The feed composition for the Toluene:Atosol mixture had 56 wt % of Toluene and 33 wt % of $C_{10}$+ products. Toluene-Atosol feed was on stream for seven days with the same catalyst that was on stream with Toluene feed for 63 days in Example 2. The feed composition is shown in greater detail in Table 4.

TABLE 4

Feed composition for 50:50 Toluene: Atosol feed.

| Feed Composition | wt % |
|---|---|
| Benzene | 0.00 |
| Toluene | 55.72 |
| Ethyl Benzene | 0.01 |
| p-Xylene | 0.00 |
| m-Xylene | 0.00 |
| Cumene | 0.02 |
| o-Xylene | 0.01 |
| n-Propyl Benzene | 0.05 |
| p-Ethyl Toluene | 0.12 |
| m-Ethyl Toluene | 0.21 |
| t-Butylbenzene | 0.02 |
| Isobutylbenzene | 0.00 |
| 1,3,5-Trimethylbenzene | 0.24 |
| sec-Butylbenzene | 0.06 |
| o-Ethyltoluene | 0.17 |
| 1,2,4-Trimethylbenzene | 1.86 |
| m-Diethylbenzene | 0.00 |
| p-Diethylbenzene | 0.00 |
| o-Diethylbenzene | 0.28 |
| 1,2,3-Trimethylbenzene | 1.35 |
| Naphthalene | 2.81 |
| 2-methylnaphthalene | 0.07 |
| 1-methylnaphthalene | 0.02 |
| Heavies | 32.60 |
| Unknown | 7.23 |

The reactor effluent composition for this feed was compared to the composition of the Toluene only feed. There was a slight change in the xylenes weight percent in the effluent, from 21-22% to 18-19%. The p-xylene/xylenes ratio stayed the same at 0.24 and the benzene percent in the effluent dropped from 21% to 6%. The toluene conversion was about 22% and the total conversion was at about a 40-43 wt % level. The temperature increased from 420° C. to 430° C. The $C_{10}$+ heavies content was reduced from 33 wt % to 15 wt %. An example of the effluent products yield obtained with the Toluene-Atosol feed on Day 4 on stream is presented in Table 5.

TABLE 5

Products yield for 50:50 Toluene: Atosol feed.

| Products Yield | wt % |
|---|---|
| Weight % of Liquid Feed | |
| Nonaromatics (wt %): | 3.12% |
| Ethylbenzene (wt %): | 1.32% |
| Toluene (wt %) | −13.24% |
| Benzene (wt %): | 5.95% |
| Xylenes (wt %): | 18.73% |
| $C_9$ Heavies (wt %): | 6.72% |
| 1,3,5-TMB | 1.52% |
| 1,2,4-TMB | 2.49% |
| 1,2,3-TMB | −0.71% |
| $C_{10}$+ Heavies (wt %): | −15.71% |
| Napthalenes (wt %) | −0.79% |
| Unknown liquid (wt %) | −6.12% |

The data in Table 4 indicates that over 13 wt % of toluene was consumed in the reaction whereas about 22% of heavies including $C_{10}$+ heavies and unknown liquids of $C_{11}$+ were consumed in the reaction, indicating that more of the lower value heavies were converted than toluene to form benzene and xylenes.

A comparison of selectivities to major products with Toluene as a feed and Toluene:Atosol as a mixed feed is shown in FIG. 6.

Various terms are used herein, to the extent a term used is not defined herein, it should be given the broadest definition persons in the pertinent art have given that term as reflected in printed publications and issued patents.

The term "activity" refers to the weight of product produced per weight of the catalyst used in a process per hour of reaction at a standard set of conditions (e.g., grams product/ gram catalyst/hr).

The term "conversion" refers to the weight percent of a reactant (e.g. toluene) that undergoes a chemical reaction. For example, $X_{Tol}$=cony of toluene (wt %)=$(Tol_{in}-Tol_{out})/Tol_{in}$.

The term "deactivated catalyst" refers to a catalyst that has lost enough catalyst activity to no longer be efficient in a specified process. Such efficiency is determined by individual process parameters. A deactivated catalyst generally requires process shut down in order for a regeneration procedure to be carried out.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

The term "niobium content of the catalyst" refers to the content of niobium metal on the catalyst by weight as a percentage of the total catalyst weight. It is the weight of the Nb elemental metal and not the entire weight of any possible Nb containing compound, such as a Nb oxide.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "rhenium content of the catalyst" refers to the content of rhenium metal on the catalyst by weight as a percentage of the total catalyst weight. It is the weight of the Re elemental metal and not the entire weight of any possible Re containing compound, such as a Re oxide.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

The term "selectivity" refers to the relative activity of a catalyst in reference to a particular compound in a mixture. Selectivity is quantified as the proportion of a particular product relative to all other products.

$S_{Bz}$=selectivity of toluene to benzene (mol %)=Benzene$_{out}$/Tol$_{converted}$ $S_{xyl}$=selectivity of toluene to xylenes (mol %)=Xylenes$_{out}$/Tol$_{converted}$ The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. In particular the combination of multiple and/or alternative embodiments discussed herein is meant to be enabled within this application. Other and further embodiments, versions and examples of the invention may be devised without departing from the basic scope thereof and the scope thereof is determined by the claims that follow.

What is claimed is:

1. A catalyst useful in the conversion of hydrocarbons comprising:
    a molecular sieve catalyst containing a group V metal and rhenium;
    wherein the molecular sieve catalyst is a mordenite zeolite that contains at least 0.0002 wt % and up to 0.3 wt % of the rhenium based on the total weight of the catalyst.

2. The catalyst of claim 1, wherein the rhenium comes from a rhenium precursor comprising one or more rhenium compounds.

3. The catalyst of claim 2, wherein the rhenium precursor is selected from the group consisting of water-soluble rhenium compounds.

4. The catalyst of claim 2, wherein the rhenium precursor is selected from the group consisting of sodium perrhenate, ammonium perrhenate, and dirhenium decacarbonyl.

5. The catalyst of claim 1, wherein the group V metal is niobium.

6. The catalyst of claim 5, wherein the niobium comes from a niobium precursor comprising one or more niobium compounds.

7. The catalyst of claim 6, wherein the niobium precursor is selected from the group consisting of water-soluble niobium compounds.

8. The catalyst of claim 6, wherein the niobium precursor is selected from the group consisting of niobium oxalate and ammonium niobate(V) oxalate.

9. The catalyst of claim 1, wherein the molecular sieve catalyst contains at least 0.005 wt % niobium based on the total weight of the catalyst.

10. The catalyst of claim 1, wherein the mordenite zeolite is a prepared without sulfiding the mordenite zeolite.

11. The catalyst of claim 1, wherein the mordenite zeolite contains at least 0.005 wt % of elemental niobium based on the total weight of the catalyst.

12. The catalysts of claim 1, wherein the at least 0.0002 wt % and up to 0.3 wt % of the rhenium contained by the mordenite zeolite is elemental Rhenium.

* * * * *